United States Patent
Imai et al.

[11] Patent Number: 5,846,904
[45] Date of Patent: Dec. 8, 1998

[54] SOIL FUMIGANT PREPARATIONS

[75] Inventors: Masao Imai, Chiba; Kanemitsu Miyama; Masaru Arai, both of Mobara; Hitoshi Shimotori; Tamotsu Asano, both of Chiba; Satoru Iwamori, Yokohama; Shohei Nozaki, Yokohama; Nobuhiro Fukuda, Yokohama, all of Japan

[73] Assignee: Mitsui Chemicals, Inc., Tokyo, Japan

[21] Appl. No.: 596,490

[22] Filed: Feb. 5, 1996

[30] Foreign Application Priority Data

| Feb. 7, 1995 | [JP] | Japan | 7-019095 |
| Jun. 22, 1995 | [JP] | Japan | 7-156241 |
| Oct. 19, 1995 | [JP] | Japan | 7-271411 |

[51] Int. Cl.$^6$ .............................. A01N 25/10; A01N 25/34
[52] U.S. Cl. ..................... 504/116; 424/405; 514/777
[58] Field of Search ................... 504/116; 71/DIG. 1; 424/405; 514/777

[56] References Cited

U.S. PATENT DOCUMENTS

| 5,116,414 | 5/1992 | Burton et al. | 71/DIG. 1 |
| 5,139,566 | 8/1992 | Zimmerman | 504/116 |
| 5,317,037 | 5/1994 | Golden et al. | 523/128 |
| 5,429,230 | 7/1995 | Hodakowski et al. | 206/205 |
| 5,436,268 | 7/1995 | Ohama et al. | 514/514 |

FOREIGN PATENT DOCUMENTS

| 50-89306 | 7/1975 | Japan |
| 62-192301 | 8/1987 | Japan |
| 1-172302 | 7/1989 | Japan |
| 6-345605 | 12/1994 | Japan |

*Primary Examiner*—S. Mark Clardy
*Attorney, Agent, or Firm*—Burns, Doane, Swecker & Mathis, L.L.P.

[57] ABSTRACT

Described are a stick-shaped soil fumigant preparation and an application method therefor. The fumigant preparation comprises a water-soluble and/or biodegradable film and a soil sterilizer and/or nematocide hermetically packed in the form of a stick with the film. The soil sterilizer and nematocide are each in a liquid form at room temperature.

The soil fumigant preparation according to the present invention remains suppressed in toxicity, volatility and irritation before application to the soil, but its active ingredient(s) are promptly released after application. In addition, the present invention makes it possible to provide a fumigant in such a form as permitting a substantial improvement in the efficiency of work by a fumigating worker and also to provide an effective application method therefor, without the need for any machine designed exclusively for fumigation.

15 Claims, 4 Drawing Sheets

F I G. 4
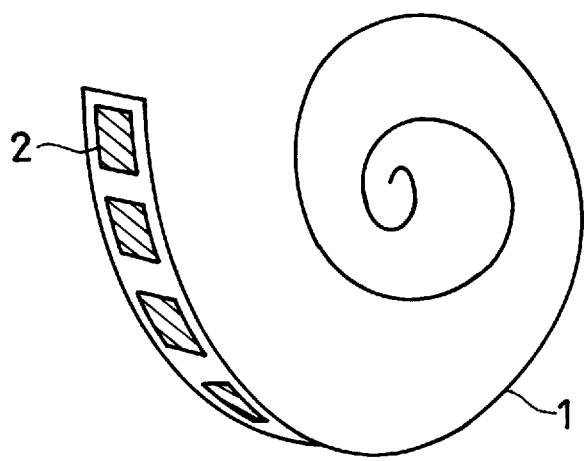
F I G. 5
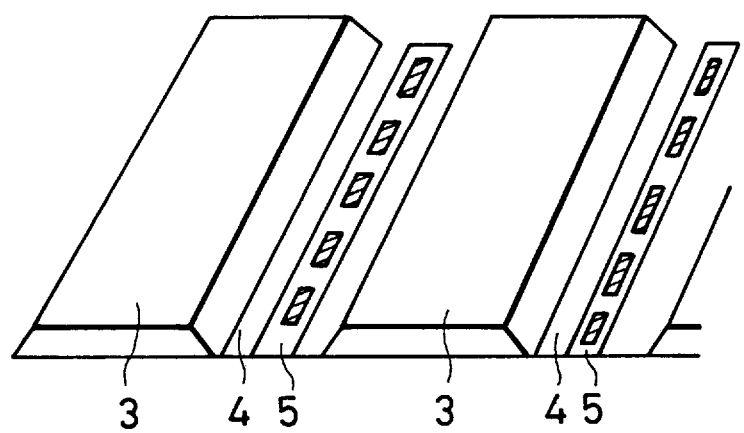
F I G. 6
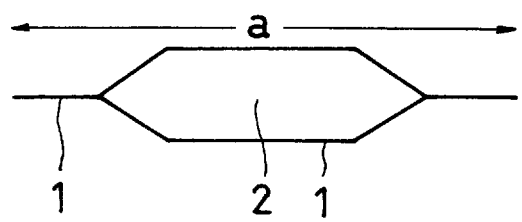

5,846,904

SOIL FUMIGANT PREPARATIONS

BACKGROUND OF THE INVENTION

1. Field of the Invention

This invention relates to soil fumigant preparations in such forms as permitting an improvement in the efficiency of work upon application to the soil and also to effective application methods thereof.

2. Description of the Related Art

To apply a soil fumigant which is in a liquid form at room temperature, such as chloropicrin, 1,3-dichloropropene, dichlorodiisopropyl ether or methyl isothiocyanate in its inherent liquid form, it is filled in a tank of a soil drenching machine and then discharged into the soil through end nozzles of the drenching machine. In this case, there is a concern about adverse effects of the fumigant on the health of a worker due to its toxicity, volatility and irritation.

With a view to preventing such chemical injury, it has recently been attempted to solidify these soil fumigants to make their application easier. As examples of such attempts, Japanese Patent Laid-Open No. 192301/1987 discloses mixing and gelatinizing chloropicrin together with dibenzylidene sorbitol and a gelation adjuster in an organic solvent and then vacuum-packing the resultant gel with a gas impermeable film, and Japanese Patent Laid-Open No. 172302/1989 discloses having liquid chloropicrin absorbed in a porous granular material and then covering the thus-treated porous granular material with a water-soluble polymer.

Soil fumigant preparations formed by such methods have both advantages and disadvantages. In particular, they are inferior in the releasability of their active ingredient in the soil. As application methods of these fumigant preparations, they are generally provided in the form of tablets and are buried in the soil by a worker by making holes one after one, placing one or more tablets in each hole and then closing the hole with the soil or by driving the tablets into the soil by an applicator designed exclusively for this purpose. The former method involves a problem of low working efficiency, while the latter is accompanied by a problem that the special applicator should be purchased additionally.

SUMMARY OF THE INVENTION

An object of the present invention is to provide a soil fumigant preparation which can overcome the above-described problems, that is, which is free from leakage of its active ingredient during its application by a worker but after being applied to the soil, can promptly and uniformly release its active ingredient into the soil. Another object of the present invention is to provide a soil fumigant preparation in a form devised to permit a substantial improvement in the efficiency of work upon fumigation and also to provide an application method therefor.

With a view to overcoming the above-described problems of the conventional art, the present inventors have conducted extensive research, leading to the completion of the present invention.

The present invention therefore provides:

(1) a stick-shaped soil fumigant preparation comprising a water-soluble and/or biodegradable film and a soil sterilizer and/or a nematocide hermetically packed in the form of a stick with the film, each of said soil sterilizer and/or said nematocide being in a liquid form at room temperature, (2) a ribbon-shaped soil fumigant preparation comprising a plurality of stick-shaped soil fumigant preparations as described above under item (1) connected together in the form of a ribbon, (3) a ribbon-shaped soil fumigant preparation as described above under item (2), wherein the ribbon-shaped soil fumigant preparation is in a folded form, (4) a ribbon-shaped soil fumigant preparation as described above under item (2), wherein the ribbon-shaped soil fumigant preparation is in a rolled form, (5) a net-shaped soil fumigant preparation comprising a plurality of ribbon-shaped soil fumigant preparations as described above under any one of items (2) to (4), said fumigant preparation having a longer axis and a shorter axis and connected together in a direction of the shorter axis in the form of a net, (6) a soil fumigant preparation as described above under any one of items (1) to (5), wherein the soil sterilizer and/or the nematocide comprises one or more of chloropicrin, 1,3-dichloropropene, dichlorodiisopropyl ether and methyl isothiocyanate, (7) a soil fumigant preparation as described above under any one of items (1) to (6), wherein the water-soluble and/or biodegradable film comprises polyvinyl alcohol (PVA), (8) a soil fumigant preparation as described above under any one of items (1) to (7), wherein the soil sterilizer and/or the nematocide has been solidified by the addition of an absorbent which can absorb the soil sterilizer and/or the nematocide, (9) a soil fumigant preparation as described above under item (8), wherein the absorbent is a water-soluble and/or biodegradable organic substance(s),

(10) a soil fumigant preparation as described above under item (9), wherein the water-soluble and/or biodegradable organic substance is starch and/or a degradation product thereof,

(11) a soil fumigant preparation as described above under item (8), wherein the absorbent(s) comprises natural earth or sand,

(12) a soil fumigant as described above under item (11), wherein the natural earth or sand comprises calcined diactomaceus earth,

(13) a soil fumigant preparation as described above under any one of items (1) to (7), wherein the soil sterilizer and/or the nematocide has been converted into a thixotropic solid form by the addition of ultrafine granular silica,

(14) a soil fumigant preparation comprising: a soil sterilizer and/or a nematocide converted into a thixotropic solid form by the addition of ultrafine granular silica as described above under item (13); and an absorbent as described above under any one of items (8) to (12),

(15) a soil fumigant preparation as described above under any one of items (2) to (14), which is suitable for application in a state left over on a soil surface or buried at a desired depth in soil,

(16) a soil fumigant preparation as described above under item (15), wherein the soil surface on which the soil fumigant preparation is left over or a surface of the soil in which the soil fumigant preparation is buried is covered with a plastic cover,

(17) a process for the production of a ribbon-shaped soil fumigant as described above under any one of items (2) to (14) by a continuous packing machine,

(18) a method for the control of a soil fungi, a nematode and/or a weed by a ribbon-shaped soil fumigant preparation as described above under any one of items (2) to (14), which comprises placing the ribbon-shaped soil fumigant preparation standstill on the soil surface,

(19) a method for the control of a soil fungi, a nematode and/or a weed by a ribbon-shaped soil fumigant preparation as described above under any one of items (2) to (14), which comprises burying the ribbon-shaped soil fumigant at a desired depth in soil,

(20) a method for the control of a soil fungi, a nematode and/or a weed by the ribbon-shaped soil fumigant preparation as described above under the item (18) or (19), which comprises covering the soil surface with a plastic cover after the ribbon-shaped soil fumigant preparation is placed standstill on the soil surface or buried in the soil, and

(21) a herbicide comprising chloropicrin as an active ingredient.

The soil fumigant preparations according to the present invention are all suppressed in toxicity, volatility and irritation before application to the soil but after application, promptly release their active ingredients into the soil. The present invention, without the need for any machine designed exclusively for fumigation, makes it possible to provide a fumigant preparation in such a form as permitting a substantial improvement in the efficiency of work by a fumigating worker and also to provide an effective application method therefor.

BRIEF DESCRIPTION OF THE DRAWINGS

FIG. 4 schematically illustrates one example of rolled soil fumigant preparations according to the present invention;

FIG. 5 schematically illustrates one application example of a ribbon-shaped soil fumigant preparation according to the present invention;

FIGS. 6 and 7 are schematic cross-sectional views of examples of the stick-shaped soil fumigant preparations according to the present invention;

Shown throughout the drawings are a water-soluble and/or biodegradable film 1, a soil sterilizer and/or nematocide 2, a length a of each stick-shaped soil fumigant preparation in the direction of its longer axis, and a length b of the stick-shaped soil fumigant preparation in the direction of its shorter axis. In FIG. 5, there are shown ridges 3, furrows 4 and ribbon-shaped soil fumigant preparations 5.

DETAILED DESCRIPTION OF THE PREFERRED EMBODIMENTS

Figure 1:
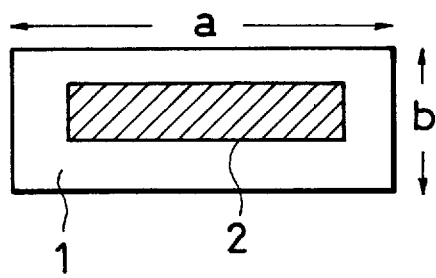
FIG. 1 is a plan view illustrating one example of stick-shaped soil fumigant preparations according to the present invention.

In the present invention, a soil fumigant is hermetically packed in the form of a stick with a water-soluble and/or biodegradable film. This preparation method allows its active ingredient to be exposed over a wider area with air via the water-soluble and/or biodegradable film, thereby achieving an improvement in the releasability of the active ingredient in soil interstices.

The term "stick-shaped soil fumigant preparation" as used herein means a soil sterilizer and/or nematocide filled in a slender stick-shaped bag or container made of a water-soluble and/or biodegradable film so that its active ingredient(s) can spread throughout the bag or container except bonded parts thereof. In a stick-shaped soil fumigant preparation with its active ingredient(s) localized at a part, the active ingredient(s) is allowed to contact only at a reduced area with the soil through a water-soluble and/or biodegradable film which preferably has gas barrier properties, thereby making it difficult to maintain a constant releasing rate and uniform concentration of the active ingredient(s) in the soil. Such a soil fumigant preparation is therefore not preferred.

A more preferred form of the term "stick-shaped" as used herein means that in a hermetically packed form, its thickness is substantially smaller relative to the area of its major surface. Incidentally, if the stick-shaped soil fumigant preparation has a significant length, that is, is in the form of a string or a tube, it may have a circular or flattened cross-section.

Although the stick-shaped soil fumigant preparation can be prepared by packing a soil sterilizer and/or nematocide as is with a water-soluble and/or biodegradable film, this preparation method involves problems in stability along the passage of time, for example, a weight loss during its storage and also in safety upon shipping or application.

In the case of the stick-shaped soil fumigant preparation, it is therefore preferred to employ an absorbent which absorbs and solidifies the soil sterilizer and/or nematocide. As the absorbent usable in the present invention, suited are those having high absorbability, permitting a prompt release of the active ingredient(s) in the gas form after application, without being kept persistently in the liquid form in the soil, having excellent storage stability in the form of preparations and being much less harmless to the environment. Chaff, peanut shells, crushed corn cores which are disclosed in Japanese Patent Laid-Open No. 345605/1994 are not desired as absorbents for the above object due to their problems from the environmental standpoint, while a soil fumigant mixed with hydrous silica such as white carbon involves a problem in storage stability.

Examples of the absorbent usable in the present invention include water-soluble organic substances and/or biodegradable organic substances having the above-described properties. Preferred examples include polysaccharides, mainly starch and/or degradation products of starch; and natural soil or sand, preferably calcined diatomaceous earth. A more detailed description will be made subsequently herein about water-soluble organic substances and/or biodegradable organic substances usable as absorbents.

A process is disclosed in Japanese Patent Laid-Open No. 89306/1975 for the preparation of a chloropicrin soil fumigant preparation having suppressed volatility. This process comprises bringing chloropicrin into contact with cyclic dextrin as a carrier in the presence of water so that chloropicrin is included in the cyclic dextrin. This process is however not practical because the amount of chloropicrin which can be included in the cyclic dextrin is too small to raise the concentration of its active ingredient in the resultant soil fumigant preparation. In addition, it takes time to have chloropicrin adsorbed on the carrier upon inclusion of chloropicrin in the carrier. When a soil fumigant preparation is formed as described above, the chloropicrin once adsorbed on the carrier cannot be released easily in the soil so that substantial time is needed until it is volatilized and released in the soil. This chloropicrin soil fumigant preparation therefore involves a further problem from the standpoint of fast-acting property.

Another process is disclosed in Japanese Patent Laid-Open No. 172302/1989, in which liquid chloropicrin is absorbed in a porous granular material, followed by covering with a water-soluble polymer. This process is accompanied with the drawbacks that it takes a significant length of time for the adsorption of chloropicrin and complex and time-consuming manufacturing steps such as absorption, filtration, coating with a water-absorbing organic material and drying are required. In this process, a zirconium compound which cannot be considered to be free of toxicity against living organisms is used as a water-absorbing organic substance so that as a preparation for outdoor use, the preparation so obtained is not necessarily be considered as a soil fumigant preparation which is much less harmless to the environment. Furthermore, in this process, a porous granular material as large as about 2 to 20 mm in diameter is used as an absorbent. Similar to the preparation disclosed in Japanese Patent Laid-Open No. 89306/1975, substantial time is needed until chloropicrin is volatilized and released in the soil, so that this process also involves a problem in fast-acting property.

Accordingly, preferred as absorbents for use in the present invention are those making it possible to raise the content of the active ingredient(s) in a preparation, to keep the production cost low, to permit simple manufacturing steps; and effectively suppress the volatility, irritation and tearing tendency of chloropicrin or the like upon sowing the preparation but once it is sowed to the soil, to promptly release the chloropicrin in the soil so that a chloropicrin or the like preparation also effective from the viewpoint of protection of the natural environment can be obtained.

Different from the conventional inclusion procedure, liquid chloropicrin or the like absorbed in an absorbent is of such a form as permitting packing just after the mixing. Immediately after the chloropicrin or like preparation so obtained is sowed, the active ingredient is promptly volatilized and released in the soil so that the chloropicrin or like preparation is fast-acting with a small residual amount of chloropicrin or the like.

In the present invention, any water-soluble and/or biodegradable organic substance can be employed as an absorbent mixable with a soil sterilizer and/or nematocide such as chloropicrin. Use of an absorbent which cannot absorb chloropicrin or the like in a large amount inevitably results in a lower content of the active ingredient(s), in other words, in a preparation of a larger size, leading to an increase in manufacturing cost and also shipping cost. Such an absorbent is therefore not suited for industrial use. Although no particular limitation is imposed on the content of the active ingredient(s) in the preparation, it is preferred from the viewpoint of commercialization to use an absorbent capable of providing a content of chloropicrin or the like as high as at least 50% for the above-mentioned reason.

As a result of an extensive investigation on water-soluble and/or biodegradable organic substances in an attempt to find those having high absorption and low persistency with respect to chloropicrin, starch and degradation products thereof have been found to be generally usable. Among them, some starch and dextrin have been ascertained to have high absorption and low persistency. Described specifically, use of potato starch is not very preferred due to its low absorption, while corn starch and solubilized starch have high absorption so that they are absorbents particularly suited in an industrial process for the production of an odor- and irritation-free chloropicrin preparation.

Concerning dextrin which is a degradation product of starch, cyclic dextrin is not so desired as an absorbent for use in an odor- and irritation-free preparation because of its low chloropicrin absorption and rather high persistency. Dextrin in which molecules of α-glucose are linked in a linear form is, on the other hand, suited in an industrial process for the production of an odor- and irritation-free chloropicrin preparation owing to its high chloropicrin absorption and low persistency in the soil.

No particular limitation is imposed on the dextrin as mentioned herein, namely, that composed of molecules of α-glucose linked in a linear form. However, preferred is a dextrin having a DE value (extent of degradation) of 2 to 40. Dextrins of higher extents of degradation, for example, those degraded to monosaccharide (α-glucose) or dissacharide are not preferred because the chloropicrin absorption becomes smaller.

For the industrial production, it is preferred to use starch or dextrin as an absorbent in a smallest possible amount to give such an amount ratio as permitting no apparent residue of liquid such as chloropicrin. This optimum mixing ratio differs with the kind of starch or dextrin to be mixed with chloropicrin or the like. When corn starch is used, for example, it is preferred to mix chloropicrin with corn starch at a ratio of 6 parts by weight to 5 parts by weight or so.

A preparation of chloropicrin or the like formed by absorbing it in such a water-soluble organic substance and/or biodegradable substance and then hermetically packing the resultant substance(s) in the form of a stick with a water-soluble and/or biodegradable film can release its active ingredient(s) promptly after being sowed in to the soil and in addition, has excellent storage stability of the absorbed ingredient(s) over a long period of time after production. For example, practically no weight loss will be observed on a chloropicrin preparation obtained by having chloropicrin absorbed in starch or dextrin and then hermetically packing the resulting starch or dextrin in the form of a stick with a PVA (polyvinyl alcohol) film, even after it is left stored at room temperature for three years.

In short, the chloropicrin preparation or the like according to the present invention is an excellent preparation having both high releasing property in the soil and high storage stability despite these properties are contradictory to each other.

It has also been found that in the case where natural earth or sand is used as an absorbent, high absorption for a soil sterilizer and/or nematocide and good releasing property for the active ingredient(s) are exhibited similar to the use of a water-soluble and/or biodegradable organic substance such as starch or dextrin. Among the earths or sands, calcined diactomaceus earth has very high absorbing ability. It can provide a content of chloropicrin as high as 80%.

It is needless to say that the preparation using natural earth or sand, a soil component, as an absorbent has no environmental problem even after application.

It is also effective, from the standpoint of continuous production of a preparation, to mix ultrafine granular silica with a liquid soil sterilizer and/or nematocide to impart thixotropic properties to the resulting mixture, because the mixture can be handled as a flowable mass so that an automatic filling and packing machine to be described subsequently herein can be applied to its filling and packing. In this case, further addition of the above-described absorbent is preferred especially from the viewpoint of the stability of the preparation.

The term "ultrafine granular silica" as used herein means (1) silicon dioxide containing no water in its molecule, which is represented by the chemical formula $SiO_2$ and (2) that represented by the chemical formula $SiO_2 \cdot nH_2O$ and called "hydrous silicon dioxide". As to the ultrafine granular silica, its primary particles have an average particle size of at least 0.07 $\mu$m but not larger than 0.5 $\mu$m and have a surface area of at least 50 $m^2/g$ but not greater than 500 $m^2/g$ as measured in accordance with the BET method. They however undergo cohesion to form secondary particles having an average particle size of at least 0.5 $\mu$m but not larger than 10 $\mu$m. Accordingly, the ultrafine granular silica used in the present invention has an average particle size of at least 0.07 $\mu$m but not larger than 10 $\mu$m. The ultrafine granular silica features a small average particle size, a large surface area, formation of a network structure through hydrogen bonds between silanol groups (SiOH) on surfaces of particles and those on surfaces of other particles, and the like.

The ultrafine granular silica, which is used for the production of solidified agrichemicals having thixotropic properties, can retain the active ingredient(s) of the agrichemicals at a content as high as about 85% or even higher so that it is a very effective carrier from the viewpoint of the production cost of preparations too.

Examples of commercially-available ultrafine granular silica usable in the present invention include "Aerosil 300" (trade name; product of Nippon Aerosil Co., Ltd.).

The amount of the absorbent can be reduced by the addition of ultrafine granular silica as an absorbent compared with the addition of the above-mentioned polysaccharide for absorption, thereby advantageously further reducing the total weight of the preparation. In the case of ultrafine granular silica, it can be added preferably in an amount of 4–15 wt. % based on the active agrichemical ingredient(s).

It is preferred to connect, as units, a plurality of stick-shaped soil fumigant preparations according to the present invention in the form of a ribbon and optionally to fold or roll up the thus-obtained ribbon-shaped soil fumigant preparation.

Especially when the ribbon-shaped soil fumigant preparation of chloropicrin or the like is so folded or rolled up into a single package as a whole, it is exposed to the air at an outermost part only, and most of the stick-formed units remain in close contact with each other inside the folded or rolled-up package so that they are very effectively shielded from the air. The ribbon-shaped soil fumigant preparation in the folded or rolled-up form is a preparation excellent in gas barrier properties so that leakage of its active ingredient(s) through a packaging material such as a PVA film can be almost completely avoided. This is one of important advantages available from forming a ribbon-shaped soil fumigant preparation into a folded or rolled-up form.

It has heretofore been the practice to make a number of small holes in a cultivated land and to bury a soil fumigant preparation in each of these small holes. The ribbon-shaped soil fumigant preparation formed of a plurality of stick-shaped soil fumigant preparations according to the present invention connected together or the soil fumigant preparation obtained by folding or rolling up the ribbon-shaped soil fumigant preparation only requires to dig a furrow of an appropriate depth (desired depth) in the field and then to lay the soil fumigant preparation so that it extends along the furrow. No applicator designed exclusively for the application of a soil fumigant applications is hence required, thereby bringing about a significant improvement in the efficiency of work.

Japanese Patent Laid-Open No. 345605/1994 briefly discloses packs produced in the form of tubular, spherical or rectangular bags from the viewpoint of economy upon processing and also attachment of these packs on a tape at constant intervals. Although not specifically disclosed, formation of individual packs and subsequent attachment thereof on a tape as described above requires an additional step for the attachment when the attachment is performed using an adhesive on the like. Furthermore, the additional use of a film or sheet as the tape is not preferred because it leads to an increase in the production cost when its production on an industrial scale is considered. Bonding of such packs on a tape one after one by heat-sealing, on the other hand, needs irksome operations, thereby making it difficult to industrially perform it. Bonding of plural packs on a film by lamination involves the potential danger that the packs may be ruptured or otherwise broken to result in leakage of the soil fumigant.

Different from a ribbon-shaped soil fumigant preparations formed by attaching individual packs on a tape by bonding or the like as disclosed in Japanese Patent Laid-Open No. 345605/1994, the term "ribbon-shaped soil fumigant preparation" as used herein with respect to the present invention means a ribbon-shaped soil fumigant preparation in which a film itself is in the form of a ribbon as a whole and the ribbon-forming film itself makes up pack portions at constant intervals along the ribbon, preferably, a ribbon-shaped soil fumigant preparation in which a plurality of packs have been formed (with the individual packs filled with an active ingredient) from a film or sheet as a raw film or sheet by using an automatic filling and continuous packing machine.

Figure 7:
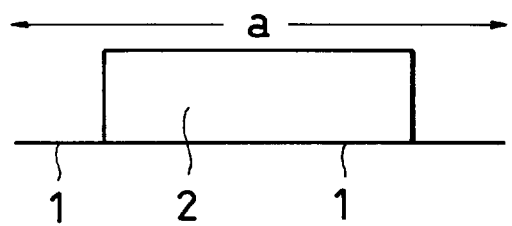

One example of the stick-shaped soil fumigant preparation according to the present invention is shown in plan in FIG. 1. A soil sterilizer and/or nematocide (which may hereinafter be referred to as "the active ingredient") 2 is hermetically packed in a water-soluble and/or biodegradable film 1. Illustrative cross-sectional views of such a stick-shaped soil fumigant preparation are schematically shown in FIGS. 6 and 7. In these examples, the thickness of the film portion with the active ingredient hermetically packed therein is sufficiently thin relative to the area of a main surface (which is shown in the plan view). It is to be noted that FIGS. 6 and 7 are merely schematic views and should not be taken as exactly representing the dimensional ratio of the thickness to the main surface. It can be understood by those skilled in the art that the shape and angle (i.e., the rising or falling angle relative to the main surface) of the portion with the active ingredient hermetically packed therein can be changed as desired.

Although no particular limitation is imposed on the size of the stick-shaped bag or container, preferred is a bag or container having a length of 3–20 cm, a width of 1–10 cm, a longer axis (a)/shorter axis (b) ratio of about 2–20, and when formed into a preparation, a thickness of about 0.3–3.0 cm.

Figure 8:
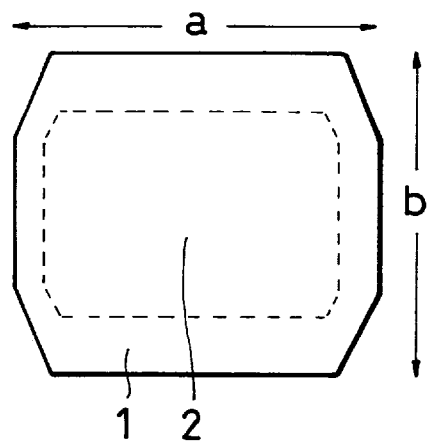
FIGS. 8, 9 and 10 are plan views illustrating examples of the stick-shaped soil fumigant preparations according to the present invention.
Figure 9:
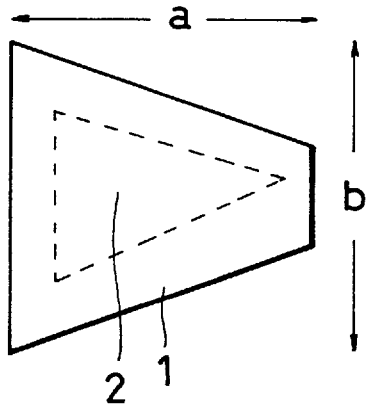
Figure 10:
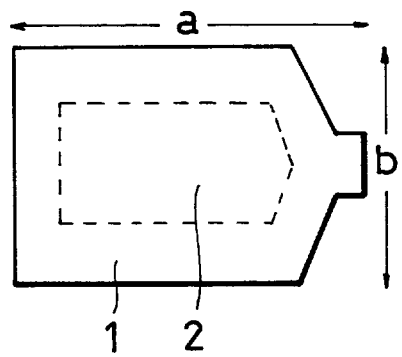

Although no particular limitation is imposed on the shape of the stick-shaped bag or container, examples of the shape as viewed in plan include polygonal shapes such as square, rectangle, triangle and hexagon; and circular, oval and bottle shapes. In addition to the example shown in FIG. 1, the other examples of the shape of the stick-shaped soil fumigant preparation are shown in plan in FIGS. 8–10. FIG. 8 shows an octagonal stick-shaped soil fumigant preparation, FIG. 9 a triangular stick-shaped soil fumigant preparation, and FIG. 10 a bottle-shaped soil fumigant preparation. Irrespective of the shape of the stick-shaped soil fumigant preparation, preferred is one having a sufficiently small thickness at the portion with the active ingredient hermetically packed therein relative to the main surface.

The thickness of the film which forms the stick-shaped bag or container differs with its material. An unduly large thickness prevents release of the active ingredient when applied to the soil, while an excessively small thickness leads to leakage of the active ingredient during storage or during application. The particularly preferred thickness is therefore from about 12.5 to 200 $\mu$m in general.

It is desired that the water-soluble and/or biodegradable film for use in the present invention has gas-barrier properties. With respect to the gas-barrier properties, the present inventors have found that, if a film having an oxygen gas permeability of 4,000 cc/atm·m$^2$·24 hr or lower is used, substantially no irritating odor of chloropicrin or the like is felt from the preparation. More preferred is to use a polyvinyl alcohol (PVA) or like film having an oxygen gas permeability of about 10 cc/atom·m$^2$·24 hr or lower so that the irritating odor of chloropicrin can be completely suppressed. Examples of the film usable in the present invention include, but are not limited to, a PVA film ("Hicellon C", trade name; product of Nichigo Film Co., Ltd.), "Pullulan film" (trade name, product of Hayashibara Sho-ji Co., Ltd.), denatured PVA film, chitin film, chitosan film, methyl cellulose film, carboxy methyl cellulose film, gelatin film and starch film. These films are used solely or in combination in layered form. These films may be laminated with water-soluble paper or fiber. A PVA film is particularly preferred for its low reactivity with the active ingredient and its easy formability into bags or containers by a packing machine.

Any soil sterilizer and/or nematocide can be used suitably in the present invention insofar as it remains in a liquid form at room temperature but readily turns into a gaseous form in the soil. Examples include, but are not limited to, chloropicrin, 1,3-dichloropropene, dichlorodiisopropyl ether and methyl isothiocyanate. They can be hermetically packed in a stick either singly or in combination.

Further, the weight of each stick-shaped soil fumigant preparation is about 1 to 20 g in view of fuming efficiency and the efficiency of work at the time of application. Needless to say, it varies depending on the kind of the fumigant, that is, the active ingredient.

No particular limitation is imposed on the kind of the packing machine useful for the industrial formation of the ribbon-shaped soil fumigant preparation of the present invention but for industrial production, preferred is an automatic filling and packing machine which is equipped with a system capable of automatically weighing the active ingredient of the soil fumigant preparation, which is in a liquid form at room temperature, and a powdery absorbent such as a water-soluble and/or biodegradable organic substance, natural earth and sand or the like.

For example, the ribbon-shaped soil fumigant preparation according to the present invention can be produced by packaging the active ingredient, the absorbent and the like in individual bags to be formed continuously, for example, by charging the active ingredient, the absorbent and the like in an automatic filling machine such as an auger feeder and, under mixing, packaging them in individual bags to be formed continuously. In this case, provision of the active ingredient with thixotropic property by the addition of ultrafine granular silica is convenient because the resultant mixture can be handled as a fluid mass and can be automatically filled.

A more specific description will hereinafter be made using chloropicrin and dextrin as an active ingredient and an absorbent by way of example.

To separately fill chloropicrin and dextrin, these ingredients are weighed in predetermined amounts by using, for example, a piston pump, a "Monopump" (trademark; manufactured by Heishin Soubi K.K.) or the like for chloropicrin and a weighing and filling machine or an auger-type filling machine for dextrin and are filled in a bag which has been formed by heat-sealing a raw PVA film at two sides, followed by heat-sealing of a remaining side, which is a filling opening, to produce a package. These procedures are repeated to produce a ribbon-shaped chloropicrin preparation. In this case, arrangement of a chute portion at the filling opening can prevent sticking of dextrin on a heat-sealed portion (i.e., on a side of the filling opening) and can hence reduce defectively-sealed preparations. It has also been found that because of the thermal fusibility and elongation of PVA, a PVA film is stretched and rendered thin to result in defectively-sealed preparations if the PVA film is driven at a heat-sealed portion by a film feeder. In this respect, it has then been found that undesired stretching of the PVA film can be prevented if a heat-sealed portion of the PVA film is used as a feeder-engaged portion. Incidentally, automatic packing with a raw PVA film can be conducted using an upright pillow-type packing maching "MC-501" (trade name; manufactured by Sanko Machinery Co., ltd.).

When chloropicrin and dextrin are simultaneously filled subsequent to their mixing, it is preferred to use an auger filling machine. An auger filling machine can fill both fluid and non-fluid powders or particles in a predetermined constant amount. Simultaneous filling can be achieved, for example, by using an auger powder filling machine manufactured by Technica Corporation. The packaging of the chloropicrin-dextrin mixture can be effected in substantially the same manner as the the above-described separate filling.

From the standpoint of the storage stability of the preparation, it is preferred for each stick-shaped preparation to be free of air.

Figure 2:
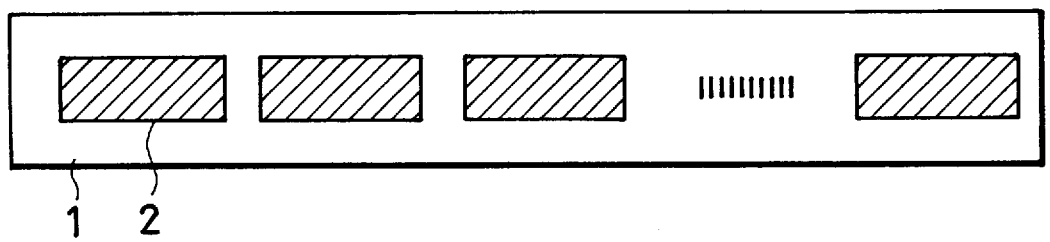
FIG. 2 is a plan view illustrating one example of ribbon-shaped soil fumigant preparations according to the present invention.

One example of the ribbon-shaped soil fumigant preparation according to the present invention is illustrated in FIG. 2. Individual stick-shaped soil fumigant units can be connected together longitudinally (i.e., in the direction of a longer axis of each unit) or laterally (i.e., in the direction of a shorter axis of each unit) or in both the directions. Connection in the longitudinal direction is however preferred because, if the ribbon-shaped soil fumigant preparation is too long in the lateral direction or has an unduly large width, the ribbon-shaped soil fumigant would not be applied easily and would not be preferred from the standpoint of the efficiency of fumigation. Although the number of individual stick-shaped soil fumigant units to be connected varies depending on the area of a field where the resulting ribbon-shaped soil fumigant preparation is to be applied, about 30 to 1,000 stick-shaped soild fumigants are generally connected.

Figure 11:
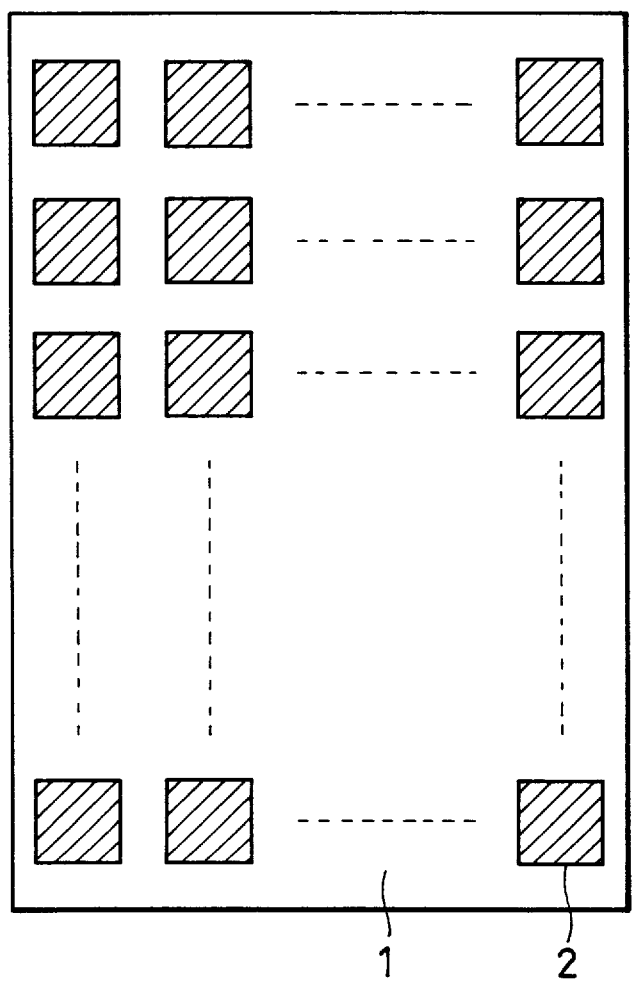
FIG. 11 is a plan view illustrating one example of net-shaped soil fumigant preparations according to the present invention.

Further, one example of the net-shaped (checkboard-patterned) soil fumigant preparation according to the present invention is depicted in FIG. 11. This net-shaped soil fumigant preparation has been formed by connecting plural ribbon-shaped soil fumigant units in the direction of shorter axes thereof. This connection can further improve the efficiency of application work.

Figure 3:
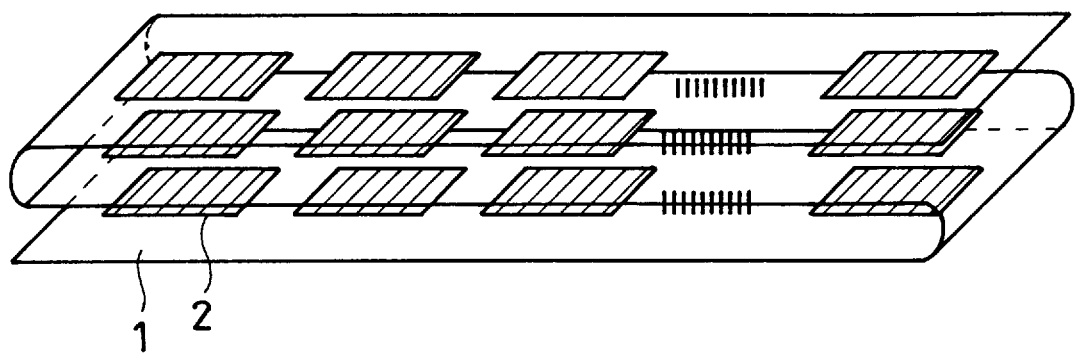
FIG. 3 is a perspective view illustrating one example of folded ribbon-shaped soil fumigants according to the present invention.

The ribbon-shaped soil fumigant preparation can be used as is. When applied in a large quantity, it is preferred to use it in a folded or rolled-up form from the standpoint of the efficiency of application or the convenience in shipping and storage. The ribbon-shaped soil fumigant preparation according to the present invention is shown in a folded form in FIG. 3 and also in a rolled form in FIG. 4, both by way of example.

The folding or rolling-up operation can be manufally performed. As an industrial production process, it is however preferred to fold the ribbon-shaped soil fumigant preparation by an automatic folding machine designed exclusively for this purpose or to wind it in the form of a roll by an automatic winding machine.

The application method of a ribbon-shaped soil fumigant preparation in a folded or rolled-up form varies depending on the kind of its active ingredient. An illustrative application method is shown in FIG. 5. Furrows 4 are made in a surface of a plowed, crushed upland field. A ribbon-shaped soil fumigant preparation 5 is placed in each furrow 4, followed by covering with soil to bury the ribbon-shaped soil fumigant preparation 5 in the soil. As an alternative, ribbon-shaped soil fumigant preparations can be left over, as are, on the surface of the plowed, crushed upland field. Further, the soil surface covering each furrow or the soil surface on which each ribbon-shaped solid fumigant preparation is placed can be covered with a plastic covering material such as a plastic film made of agricultural polyvinyl chloride, polyethylene or the like.

In the case of a ribbon-shaped soil fumigant of chloropicrin, for example, the ribbon-shaped soil fumigant preparation can be applied by digging a furrow to a depth of about 10 to 15 cm in a surface of a plowed, crushed upland field and burying the ribbon-shaped soil fumigant preparation in a linearly-extended form in the furrow or by laying the ribbon-shaped soil fumigant in a linearly-extended form on the surface of the plowed, crushed upland field and covering the soil surface with a plastic film.

Incidentally, it has also been found surprisingly that application of the soil fumigant preparation hermetically packed as described above is effective not only for the control of diseases and nematodes but also for the control of weeds.

As a result of a further detailed investigation, it has also been found that, when used as a herbicide, herbicidal effects can be exhibited against troublesome weeds such as crabgrass (*Digitaria adscendes*), amaranth (*Amaranthus viridis*), foxtail (*Setaria viridis*), common cocklebar (*Xanthium strumarium L.*) common lambsquarters (*Chenopodium album L.*), and smartweed (*Polygonum Blumei Heisn.*) not only by the chloropicrin preparation hermetically packed as described above but also by active ingredients themselves.

Weed control making use of a herbicide composed of chloropicrin can be conducted as will be described next. Even when starch with chloropicrin absorbed therein or an unsealed glass container with chloropicrin stock contained therein was left over on a surface of soil, on which seeds of the above-mentioned troublesome weeds had been sowed, and the soil surface was then covered by a covering material such as an agricultural polyvinyl chloride or polyethylene film, the above-mentioned troublesome weeds did not germinate at all. When chloropicrin stock was simply drenched in soil, the active liquid ingredient however spread in the soil and was adsorbed in a not a little amount in the soil. Its inherent control effects against troublesome weeds were not observed to any significant extent.

Use of the soil fumigant preparation according to the present invention has numerous merits over the conventional method in which a liquid soil fumigant is drenched in soil. A desription will be made taking as an example chloropicrin which is used widely as a soil fumigant. Although liquid chloropicrin requires hole-by-hole drenching at intervals or 30 cm by using a soil drenching machine designed exclusively for this purpose, it is only necessary for the ribbon-shaped soil fumigant preparation according to the present invention to be simply placed on a soil surface or buried in a linear form in soil. The efficiency of work can therefore be improved significantly. Further, liquid chloropicrin has strong irritation and decryogenicity, inherently gives pain upon fumigation and in addition, involves problems in safety and hygiene. In contrast, the ribbon-shaped solid fumigant preparation according to the present invention is substantially free of irritation and can be applied in extreme safety. Moreover, when liquid chloropicrin is applied to soil, not a little portion thereof is instantaneously adsorbed on soil particles so that spreading of gas as the active ingredient through the soil is suppressed. In the case of a ribbon-shaped soil fumigant preparation with chloropicrin carried on a solid absorbent, its application to soil however permits gasfication and spreading of chloropicrin throughout interstices of the soil without adsorption on soil particles as the chloropicrin is carried on the solid adsorbent. Therefore the ribbon-shaped soil fumigant preparation with the active ingredient contained in the same amount therein can effectively control diseases, nematodes and weeds over a wider area.

A specific description will hereinafter be made taking chloropicrin as an illustrative soil sterilizer and/or nematocide and a polyvinyl alcohol (PVA) film as a water-soluble and/or biodegradable film.

Chloropicrin has a melting point of −64° C., a boiling point of 112° C. and a specific gravity of 1.651 and is in the form of a clear colorless liquid substantially insoluble in water. Although chloropicrin may be hermetically packed as is with a PVA film to form a stick-shaped preparation, a stick-shaped preparation is generally formed by adding an absorbent having high chloropicrin-absorbing ability, for example, starch or a hydrolysate thereof to chloropicrin from the standpoint of the stability of the preparation, stirring and solidifying the resultant mixture, and then hermetically packing the thus-obtained mixture with a PVA film.

For industrial production, starch or its hydrolysate which is employed as an absorbent in an odor- and irritation-free chloropicrin preparation is preferably used in a minimum amount to give such a weight ratio that chloropicrin liquid apparently does not remain. This optimal mixing ratio varies depending on the kind of the starch or the hydrolysate thereof to be mixed with chloropicrin. When corn starch is used, for example, it is preferred to mix chloropicrin and corn starch at a ratio of 6 parts by weight to 5 parts by weight or so.

Use of a water-soluble and/or biodegradable organic substance, for example, starch as an absorbent is preferred not only for the fact that it is compatible with the environment after application but also from the standpoint of the stability of the preparation. When chloropicrin is simply absorbed, as in the conventional art, in an inorganic carrier which can firmly adsorb and include chloropicrin, the chloropicrin is not released from the carrier when the preparation is actually applied in soil. Accordingly, the desired effects are not exhibited. Use of a water-soluble and/or biodegradable absorbent having high chloropicrin-absorbing ability such as starch can bring about such advantageous effects that the resulting preparation remains stable during storage or shipping but, when applied to soil, starch or the like undergoes degradation to readily release chlropicrin into soil.

Regarding the production of a ribbon-shaped chloropicrin preparation by continuous packing of stick-shaped chloropicrin preparation units on an automatic filling and packing machine, a description will be made based on an example. There are however other methods for continuously packing stick-shaped soil fumigant units to form a ribbon-shaped soil fumigant preparation. Needless to say, the ribbon-shaped soil fumigant preparation according to the present invention should not be considered to be producible only by the exemplified method.

PVA bags are continuously formed by heat-sealing each bag at three sides thereof on an automatic filling and packing machine, concurrently filling chloropicrin and corn starch by a different weighing and filling machine in each PVA bag sealed at the three sides thereof, and then heat-sealing the filling opening. As an alternative, it is also possible to mix chloropicrin with corn starch into a mixture having thixotropic property and then filling the mixture by a weighing and filling machine.

The ribbon-shaped chloropicrin preparation, which has been formed continuously as described above, is then folded by a folding machine designed exclusively for this purpose or wound in the form of a roll by an automatic winding machine designed exclusively for this purpose.

No particular weight limitation is imposed on the individual stick-shaped chloropicrin preparations as the constituent units of the rolled or ribbon-shaped chloropicrin preparation produced as described above. From the standpoint of readiness, effectiveness and the like of application work, stick-shaped chlorpicrin preparation units containing chloropicrin in an amount of from 20 g to 1 g, preferably 10 g to 2 g, more preferably about 5 g per unit are preferred.

Although no particular limitation is imposed on the size of each stick-shaped chloropicrin preparation unit, the size may be, for example, about 10 cm in length and about 4 cm in width when each preparation unit is filled with about 5 g of chlorpicrin.

To store the roll-shaped, ribbon-shaped or stick-shaped chloropicrin preparation for a long period of time, it is preferred to cover or hermetically pack it further with a moistureproof sheet or film having high gas barrier properties. Preferred as such a film is, for example, a "Zekron" film having an oxygen gas permeability of 20 cc/atm·m$^2$·24 hr or lower (product of Mitsui Toatsu Chemicals Inc.).

The PVA film of the preparation produced as described above is degraded by water in soil, so that chloropicrin inside the film is released to effect fumigation of soil.

The present invention will hereinafter be described more specifically by the following examples.

EXAMPLE 1

Corn starch (500 parts by weight) was weighed on a powder weighing filler. On the side, 600 parts by weight of chloropicrin were weighed on a liquid weighing filler.

The PVA film (a rolled 10 cm×300 m PVA film, thickness: 40 μm; all PVA films to be recited hereinafter had the same thickness), was heat-sealed at desired locations by an automatic filling and packing machine, whereby PVA bags heat-sealed at three sides thereof were automatically produced one after another. The PVA bags were 10 cm long and 4 cm wide in internal dimensions and were continuously formed at a rate of 30 bags/minute.

After the PVA films were sealed at the three sides, 5 parts by weight of the corn starch were filled in the thus-obtained bag by the powder weighing filler, followed by the addition of 6 parts by weight of the chloropicrin by the liquid weighing filler. An opening of the bag, through which the chloropicrin had been added, was closed by heat-sealing. The resulting stick-shaped chloropicrin preparation was 12 cm in length, 5 cm in width and 0.7 cm in thickness. The above procedures were repeated continuously, whereby a ribbon-shaped chloropicrin preparation was manufactured.

The ribbon-shaped chloropicrin preparation continuously formed as described above was wound into a roll by an automatic winder designed exclusively for this purpose, whereby a rolled chloropicrin preparation was formed. No irritating odor of chloropicrin was found to be given off from the so-obtained preparation.

Further hermetic packaging of the preparation with "Zekron" films (trade name; product of Mitsui Toatsu Chemicals Inc.) having high gas barrier properties allowed it to remain stable as no external change was observed thereon even after it had been stored at room temperature for one year.

EXAMPLE 2

One hundred parts by weight "Isolite" (trade name, calcined diatomaceous earth produced by Isolite Insulating Products Co., Ltd.) were weighed on a powder weighing filler. On the side, 600 parts by weight of methyl isothiocyanate were weighed on a liquid weighing filler.

The PVA film (a rolled 10 cm×300 m PVA film) was heat-sealed at desired locations by an automatic filling and packing machine, whereby PVA bags heat-sealed at three sides thereof were automatically produced one after another. The PVA bags were 10 cm long and 4 cm wide in internal dimensions and were continuously formed at a rate of 30 bags/minute.

After the PVA film was sealed at the three sides, 1 part by weight of Isolite was filled in the thus-obtained bag on the powder weighing filler, followed by the addition of 6 parts by weight of the methyl isothiocyanate on the liquid weighing filler. An opening of the bag, through which the methyl isothiocyanate had been added, was closed by heat-sealing. The resulting stick-shaped methyl isothiocyanate preparation was 12 cm in length, 5 cm in width and 0.5 cm in thickness.

The above procedures were repeated continuously, whereby a ribbon-shaped methyl isothiocyanate preparation was manufactured. The ribbon-shaped methyl isothiocyanate preparation continuously formed as described above was folded by an automatic folding machine designed exclusively for this purpose, whereby a folded methyl isothiocyanate preparation was formed. No irritating odor of methyl isothiocyanate was found to be given off from the so-obtained preparation.

Further hermetic packaging of the preparation with "Zekron" films (trade name; product of Mitsui Toatsu Chemicals Inc.) having a high gas barrier property allowed it to remain stable as no external change was observed thereon even after it had been stored at room temperature for one year.

EXAMPLE 3

Corn starch (100 parts by weight) was weighed on a powder weighing filler. On the side, 30 parts by weight of "Aerosil 300" (trade name; product of Nippon Aerosil Co., Ltd.) as ultrafine granular silica and 600 parts by weight of 1,3-dichloropropene were mixed under stirring to obtain a solid mixture having thixotropic properties. The resulting mixture was weighed on a liquid weighing filler.

The PVA film (a rolled 10 cm×300 m PVA film) was heat-sealed at desired locations by an automatic filling and packing machine, whereby PVA bags heat-sealed at three sides thereof were automatically produced one after another. The PVA bags were 10 cm long and 4 cm wide in internal dimensions and were continuously formed at a rate of 30 bags/minute.

After the PVA film was sealed at the three sides, 1 part by weight of the corn starch was filled in the thus-obtained bag on the powder weighing filler. Under fluidization, 6 parts by weight of the solid-state 1,3-dichloropropene having thixotropic properties were thereafter added by the liquid weighing filler. An opening of the bag, through which the 1,3-dichloropropene had been added, was closed by heat-sealing. The resulting stick-shaped 1,3-dichloropropene preparation was 12 cm in length, 5 cm in width and 0.2 cm in thickness. The above procedures were repeated continuously, whereby a ribbon-shaped 1,3-dichloropropene preparation was manufactured.

The ribbon-shaped 1,3-dichloropropene preparation continuously formed as described above was wound up into a roll by an automatic winder designed exclusively for this purpose, whereby a rolled 1,3-dichloropropene preparation was formed. No irritating odor of 1,3-dichloropropene was found to be given off from the so-obtained preparation.

Further hermetic packaging of the preparation with "Zekron" films (trade name; product of Mitsui Toatsu Chemicals Inc.) having high gas barrier properties allowed it to remain stable as no external change was observed thereon even after it had been stored at room temperature for one year.

EXAMPLE 4

Dextrin (80 parts by weight) was weighed on a powder weighing filler. On the side, 25 parts by weight of "Aerosil 300" (trade name; product of Nippon Aerosil Co., Ltd.) as ultrafine granular silica and 500 parts by weight of dichlorodiisopropyl ether were mixed under stirring to impart thixotropic properties to the resulting mixture. The resulting mixture was weighed on a liquid weighing filler.

The PVA film (a rolled 10 cm×300 m PVA film) was heat-sealed at desired locations by an automatic filling and packing machine, whereby PVA bags heat-sealed at three sides thereof were automatically produced one after another. The PVA bags were 10 cm long and 4 cm wide in internal dimensions and were continuously formed at a rate of 30 bags/minute.

After the PVA film was sealed at the three sides, 0.8 part by weight of dextrin was filled in the thus-obtained bag on the powder weighing filler, followed by the addition of 5 parts by weight of the dichlorodiisopropyl ether having thixotropic properties on the liquid weighing filler. An opening of the bag, through which the dichlorodiisopropyl ether had been added, was closed by heat-sealing. The resulting stick-shaped dichlorodiisopropyl ether preparation was 12 cm in length, 5 cm in width and 0.3 cm in thickness. The above procedures were repeated continuously, whereby a ribbon-shaped dichlorodiisopropyl ether preparation was manufactured.

The ribbon-shaped dichlorodiisopropyl ether preparation continuously formed as described above was wound up into a roll by an automatic winder designed exclusively for this purpose, whereby a rolled dichlorodiisopropyl ether preparation was formed. No irritating odor of dichlorodiisopropyl ether was found to be given off from the so-obtained preparation.

Further hermetic packaging of the preparation with "Zekron" films (trade name; product of Mitsui Toatsu Chemicals Inc.) having high gas barrier properties allowed it to remain stable as no external change was observed thereon even after it had been stored at room temperature for one year.

Using the soil fumigant preparations obtained in Examples 1–4, their changes in form were studied. First, a furrow was made to a depth of 15 cm from a soil surface. The soil fumigant preparations were placed in the furrow and then covered with soil. Twenty four hours later, the soil was dug up and the preparations were observed for any changes in form. As a result, it was found that the PVA films on the surfaces of each of the preparations had been dissolved and that the active ingredient of the soil fumigant in the preparation had been released in the soil. Comparative Example 1

In accordance with Example 1 of Japanese Patent Laid-Open No. 192301/1987, a solid-form chloropicrin preparation was formed.

Described specifically, formed was a solid-form chloropicrin preparation having the following composition:

| | |
|---|---|
| Chloropicrin | 70 parts |
| Xylene | 10 parts |
| Chloroprene rubber | 1 part |
| Diethylene glycol diethyl ether | 3 parts |
| Caustic potash-alcohol solution | 0.3 part |
| Antioxidant | 0.04 part |
| 25% Dibenzylidene sorbitol | |
| N-methylpyrrolidone solution | 16 parts |

To the resulting preparation, petaloid magnesium silicate powder was sprayed, followed by vacuum packing with PVA films.

No chloropicrin odor was felt at all either from the preparation.

TEST 1

In a field, the soil was plowed and harrowed by a tractor to a depth of 20 cm. An area of 120 cm in width and 600 cm in length was used as each experimental plot. The ribbon-shaped soil fumigant formed according to Example 1, which contained 2.5 ml of liquid chloropicrin per one stick, was placed over 500 cm on the said surface or at a depth of 15 cm from the soil surface. As a control, commercially-available chloropicrin liquid and chloropicrin tablets (products of Nankai Chemical Industry Co., Ltd.) were used. The chloropicrin liquid was drenched to the depth of 15 cm from the soil surface at intervals of 30 cm by 5 ml/hole over 500 cm. On the other hand, the chloropicrin tablets were buried one by one at the depth of 15 cm from the soil surface at intervals of 20 cm over 500 cm. At places predetermined horizontal distance apart from the respective fumigant-treated spots, wheat seeds infected with *Fusarium oxysporum f.sp. lycoersici* which had been cultured thereon in advance were buried at the depth of 10 cm, followed by the broadcast sowing of seeds of large crabgrass and redroot pigweed on the soil surface. After that, the soil surface was covered with a polyethylene film of 0.02 mm in thickness. In addition, air was periodically sampled at a point 20 cm horizontally apart from a fumigant-treated spot and 10 cm deep from the soil surface and its chloropicrin gas concentration was measured by high performance liquid chromatography. On the 14th days after the treatment, the polyethylene film cover was removed and the buried wheat seeds were dug out. The viability of *Fusarium oxysporum f.sp. lycoersici* in each wheat seed was determined on a petri dish. The degrees of germination of the large crabgrass and redroot pigweed seeds were also observed. The results are shown in Tables 1–4.

TABLE 1

Viability of *Fusarium oxysporum* f.sp. *lycoersici*

| | Horizontal distance from treated spot (cm) | | | | | |
|---|---|---|---|---|---|---|
| Sample | 0 | 10 | 20 | 30 | 40 | 50 |
| Ribbon-shaped chloropicrin (treated at the depth of 15 cm from the soil surface) | − | − | − | − | ± | + |
| Ribbon-shaped chloropicrin (treated on the soil surface) | − | − | − | − | − | ± |
| Chloropicrin liquid | − | − | + | ++ | ++ | + |
| Chloropicrin tablets | + | ++ | ++ | ++ | ++ | ++ |
| Control (no chloropicrin was applied) | ++ | ++ | ++ | ++ | ++ | + |

−: completely dead, ±: partially living, ++: living at the same degree as control

TABLE 2

Degree of germination of weed (large crabgrass)

| | Horizontal distance from treated spot (cm) | | | | | |
|---|---|---|---|---|---|---|
| Sample | 0 | 10 | 20 | 30 | 40 | 50 |
| Ribbon-shaped chloropicrin (treated at the depth of 15 cm from the soil surface) | − | − | − | − | ++ | + |
| Ribbon-shaped chloropicrin treated on the soil surface) | − | − | − | − | − | − |
| Chloropicrin liquid | − | − | − | + | ++ | + |
| Chloropicrin tablets | − | − | − | ++ | ++ | + |
| Control (no chloropicrin was applied) | ++ | ++ | ++ | ++ | ++ | + |

−: completely dead, ±: partially living, ++: living at the same degree as control

TABLE 3

Degree of germination of weed (redroot pigweed)

| | Horizontal distance from treated spot (cm) | | | | | |
|---|---|---|---|---|---|---|
| Sample | 0 | 10 | 20 | 30 | 40 | 50 |
| Ribbon-shaped chloropicrin (treated at the depth of 15 cm from the soil surface) | − | − | − | − | − | + |
| Ribbon-shaped chloropicrin (treated on the soil surface) | − | − | − | − | − | − |
| Chloropicrin liquid | − | − | − | − | ++ | + |
| Chloropicrin tablets | − | − | − | − | ++ | + |
| Control (no chloropicrin was applied) | ++ | ++ | ++ | ++ | ++ | + |

−: completely dead, ±: partially living, ++: living as the same degree as control

TABLE 4

Chloropicrin gas concentration in the soil

| | After treatment (days) | | | |
|---|---|---|---|---|
| Sample | 1 | 3 | 7 | 14 |
| Ribbon-shaped chloropicrin (treated at the depth of 15 cm from the soil surface) | 19,000 | 3,000 | 430 | 0 |
| Ribbon-shaped chloropicrin (treated on the soil surface | 35,000 | 3,300 | 200 | 0 |
| Chloropicrin liquid | 8,500 | 790 | 0 | 0 |
| Chloropicrin tablets | 2,200 | 69 | 0 | 0 |
| Control (no chloropicrin was applied) | 0 | 0 | 0 | 0 |

* Numerals in the table show gas concentrations (ppm).

Incidentally, the machine packing applicabilities of two PVA films, one being 40 $\mu$m in thickness and the other being 80 $\mu$m in thickness, were studied.

As a result, it was found that compared with the 40 $\mu$m thick PVA film, the 80 $\mu$m thick PVA film has superior heat-sealing properties and can provide highly hermetic packages with better productivity under milder conditions.

What is claimed is:

1. A stick-shaped soil fumigant preparation comprising polyvinyl alcohol (PVA) film, a soil sterilizer which is in a liquid form at room temperature and/or a nematocide which is in a liquid form at room temperature, and a dextrin having a DE value (extent of degradation) of 2 to 40, the soil sterilizer and/or the nematocide being absorbed in the dextrin, and hermetically packed in the form of a stick with the PVA film.

2. A ribbon-shaped soil fumigant preparation comprising a plurality of stick-shaped soil fumigant preparations as defined in claim 1 connected together in the form of a ribbon, wherein the ribbon-shaped soil fumigant preparation is in a folded form.

3. A ribbon-shaped soil fumigant preparation comprising a plurality of stick-shaped soil fumigant preparations as defined in claim 1 connected together in the form of a ribbon, wherein the ribbon-shaped soil fumigant preparation is in a rolled form.

4. A soil fumigant preparation according to claim 1, wherein the soil sterilizer and/or the nematocide comprises one or more of chloropicrin, 1,3-dichloropropene and dichlorodiisopropyl ether.

5. A ribbon-shaped soil fumigant preparation according to claim 3, wherein the soil sterilizer and/or the nematocide comprises one or more of chloropicrin, 1,3-dichloropropene and dichlorodiisopropyl ether.

6. A ribbon-shaped soil fumigant preparation according to claim 3, wherein the soil sterilizer and/or the nematocide comprises one or more of chloropicrin, 1,3-dichloropropene and dichlorodiisopropyl ether.

7. A method for the control of a soil fungi, a nematode and/or a weed by the ribbon-shaped soil fumigant according to claim 2, which comprises leaving the ribbon-shaped soil fumigant preparation on a soil surface.

8. A method for the control of a soil fungi, a nematode and/or a weed by the ribbon-shaped soil fumigant according to claim 3, which comprises leaving the ribbon-shaped soil fumigant preparation on a soil surface.

9. A method for the control of a soil fungi, a nematode and/or a weed by the ribbon-shaped soil fumigant according to claim 2, which comprises burying the ribbon-shaped soil fumigant preparation at a desired depth in soil.

10. A method for the control of a soil fungi, a nematode and/or a weed by the ribbon-shaped soil fumigant according to claim 3, which comprises burying the ribbon-shaped soil fumigant preparation at a desired depth in soil.

11. A method according to claim 7 for the control of a soil fungi, a nematode and/or a weed, further comprising covering the soil surface with a plastic cover after the ribbon-shaped soil fumigant preparation is placed on the soil surface.

12. A method according to claim 8 for the control of a soil fungi, a nematode and/or a weed, further comprising covering the soil surface with a plastic cover after the ribbon-shaped soil fumigant preparation is placed on the soil surface.

13. A method according to claim 9 for the control of a soil fungi, a nematode and/or a weed, further comprising covering a surface of the soil with a plastic cover after the ribbon-shaped soil fumigant preparation is buried in the soil.

14. A method according to claim 10 for the control of a soil fungi, a nematode and/or a weed, further comprising covering a surface of the soil with a plastic cover after the ribbon-shaped soil fumigant preparation is buried in the soil.

15. The stick-shaped soil fumigant preparation according to claim 1 wherein the soil sterilizer and/or nematocide is present in an amount of at least 50% by weight of the preparation.

* * * * *